US010813608B2

(12) United States Patent
Martinez Ferreira et al.

(10) Patent No.: US 10,813,608 B2
(45) Date of Patent: Oct. 27, 2020

(54) METHOD AND SYSTEMS FOR A MOBILE IMAGING SYSTEM

(71) Applicant: General Electric Company, Schenectady, NY (US)

(72) Inventors: Carlos Martinez Ferreira, Paris (FR); Diane Blamaud, Eragny (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 127 days.

(21) Appl. No.: 16/150,041

(22) Filed: Oct. 2, 2018

(65) Prior Publication Data

US 2020/0100738 A1 Apr. 2, 2020

(51) Int. Cl.
*A61B 6/00* (2006.01)

(52) U.S. Cl.
CPC .......... *A61B 6/4405* (2013.01); *A61B 6/4441* (2013.01); *A61B 6/4458* (2013.01)

(58) Field of Classification Search
CPC .... A61B 6/4405; A61B 6/4441; A61B 6/4458
See application file for complete search history.

(56) References Cited

U.S. PATENT DOCUMENTS

| 8,992,083 | B2 | 3/2015 | Moulin et al. | |
|---|---|---|---|---|
| 2012/0053459 | A1* | 3/2012 | Eilers | A61B 8/0858 600/440 |
| 2012/0153135 | A1* | 6/2012 | Ishizuka | G01D 5/244 250/231.18 |
| 2013/0144171 | A1* | 6/2013 | Watson | A61B 8/10 600/452 |
| 2014/0009741 | A1* | 1/2014 | Levien | A61B 3/102 351/206 |

FOREIGN PATENT DOCUMENTS

| DE | 19915180 | 9/2002 |
|---|---|---|
| DE | 19915180 A1 | 9/2002 |

OTHER PUBLICATIONS

European application No. 19200658.3 filed Sep. 30, 2019, Search Report dated Feb. 18, 2020, 8 pages.

* cited by examiner

*Primary Examiner* — Mark R Gaworecki
(74) *Attorney, Agent, or Firm* — McCoy Russell LLP

(57) ABSTRACT

Various methods and systems are provided for determining the position of a mobile imaging system. One example system includes a first angular sensor coupled to a reference point and configured to measure a first angle of rotation relative to the reference point, a linear sensor coupled between the reference point and the mobile imaging system and configured to measure a distance between the reference point and the mobile imaging system, the linear sensor coupled to the first angular sensor with its string axis perpendicular to and intersecting a rotational axis of the first angular sensor, and a second angular sensor configured to measure a second angle of rotation relative to the mobile imaging system.

20 Claims, 8 Drawing Sheets

METHOD AND SYSTEMS FOR A MOBILE IMAGING SYSTEM

FIELD

Embodiments of the subject matter disclosed herein relate to a position detector for a mobile imaging system.

BACKGROUND

Radiographic imaging systems may be used in various applications, including medical and industrial applications. In a medical environment, a radiographic imaging device may provide a non-invasive means of imaging tissue and bone of a patient. The imaging device may comprise a swing arm coupled to a control unit, and a display monitor either attached to or arranged separated from the control unit. The swing arm (e.g., C-arm) may include an x-ray source positioned at one end of the arm, and a detector positioned on another end of the arm. A clearance may be provided between the x-ray source and detector to receive an object, such as a portion of the patient's body, which may be irradiated with radiation from the x-ray source. Upon irradiating the object, the x-ray radiation penetrates the object, before being captured by the detector on the other end of the object. By penetrating the object placed between the source and detector, the x-rays enable an image of the object to be captured and relayed to the display monitor, where the image may be displayed or stored and retrieved later.

The imaging device may be mounted on a mobile unit that is configured to move about a room within the medical environment, such as an operating room. By mounting the imaging device on a mobile unit, the imaging device may be moved to image a patient during certain aspects of a medical procedure, and moved out of proximity of the patient during other aspects of the medical procedure, thereby providing imaging on demand but still allowing for patient access. Such imaging devices may be relatively heavy. Further, constraints may be placed on where and how the imaging device can be moved due to other equipment in the room and the need to maintain a sterile environment. Thus, the mobile unit on which the imaging device is mounted may be configured to move automatically or semi-automatically along one or more predetermined paths.

BRIEF DESCRIPTION

In one embodiment, a system for determining a position of a mobile imaging system may include a first angular sensor coupled to a reference point and configured to measure a first angle of rotation relative to the reference point, a linear sensor coupled between the reference point and the mobile imaging system and configured to measure a distance between the reference point and the mobile imaging system, the linear sensor coupled to the first angular sensor with its string axis perpendicular to and intersecting a rotational axis of the first angular sensor, and a second angular sensor configured to measure a second angle of rotation relative to the mobile imaging system.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
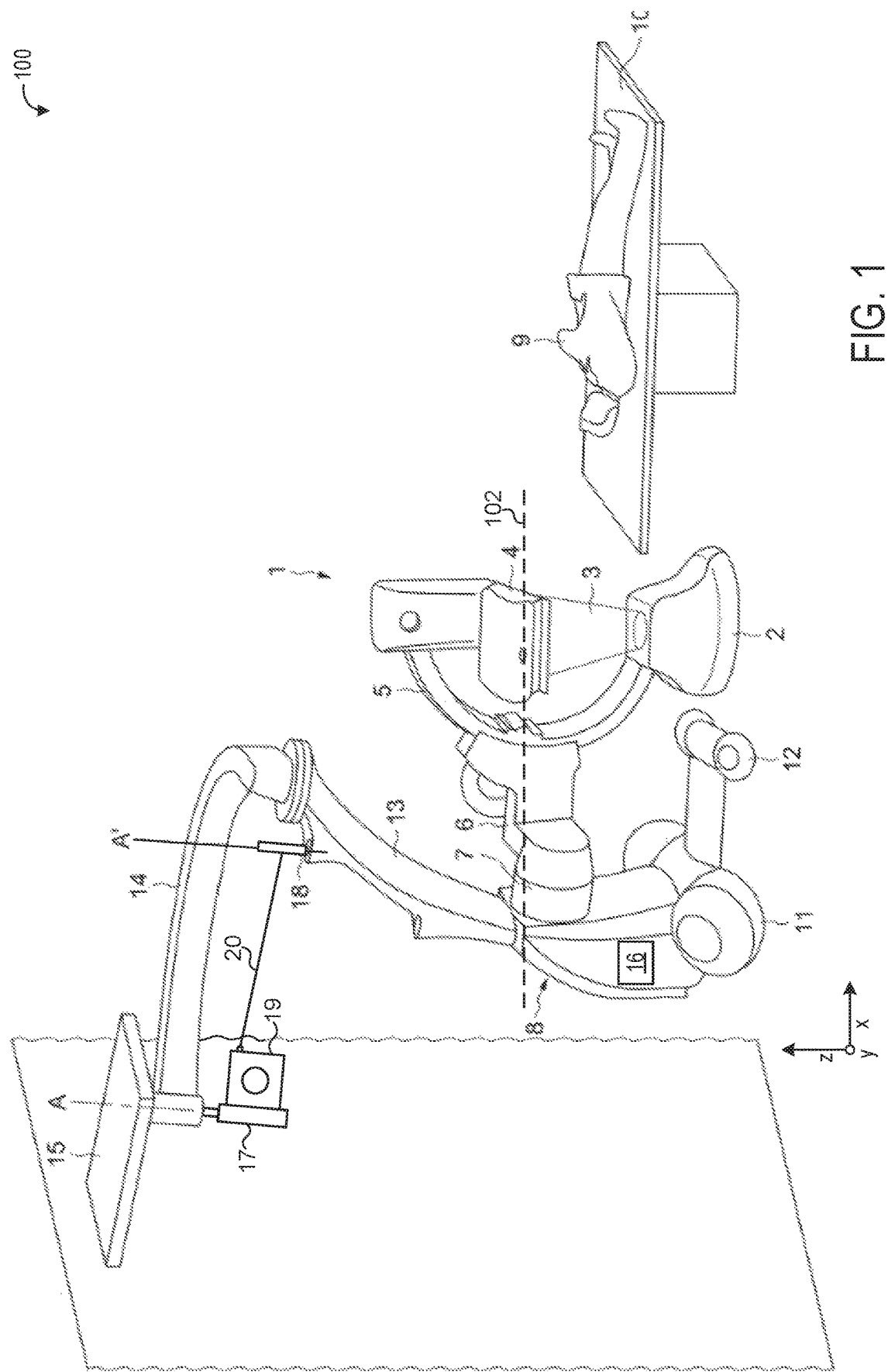
FIG. 1 is a schematic view of a mobile imaging system in the form of an x-ray system including a C-arm with an x-ray source positioned above an x-ray detector.

FIG. 1 is a perspective view 100 of a mobile imaging system 1 for three-dimensional (3D) medical imaging according to one exemplary, but non-limited, embodiment of the disclosure. The mobile imaging system 1 is configured to perform image acquisition of an object to be studied, for example a part of a patient body. In the example shown in FIG. 1, the mobile imaging system 1 is an x-ray imager, but other types of imaging modalities are possible.

Mobile imaging system 1 includes an imaging assembly having an x-ray tube 2, capable of emitting a beam 3 of x-rays in an emission direction, and an x-ray detector 4 placed at the two mutually opposed ends of an arm 5, which in the example presented herein is in the form of an arch (e.g., a C-arm), so that the x-rays emitted by the tube 2 are incident on the detector 4.

The imaging assembly is mounted on a movable platform that includes a base assembly 8 and various arms coupled thereto. The arm 5 is mounted so as to slide on a second arm 6 mounted rotatingly on a fixed support 7, itself mounted on the base assembly 8. The base assembly 8 includes an automatic mobile device operable to move across the floor of an operating or examination room. The mobile imaging system 1 includes a central axis 102 that intersects a point where the second arm 6 couples to the fixed support 7 and also intersects a point where arm 5 interfaces with second arm 6.

Therefore, the support 7, the rotating arm 6, and the arm 5 are all articulated relative to one another, around and relative to the central axis 102, so that the imaging assembly can move in three dimensions and thus produce images of an anatomy to be examined from various angles of incidence.

During a radiography imaging session, the tube 2 and the detector 4 are brought to face an area of interest in the body 9 of a patient laid out on an examination table 10 so that, when the region of interest is interposed between the x-ray tube 2 and the detector 4, the region of interest is irradiated by the x-rays and the detector 4 produces data representative of characteristics of the interposed region of interest.

The mobile device of the base assembly 8 comprises, in the exemplary embodiment shown, a rolling system comprising two lateral drive wheels 11 placed at the rear, and two free front wheels 12, the drive wheels being associated with a driving unit comprising one or more motors, such as a steering motor and/or one or more driving motors. The mobile device of the base assembly 8 further includes a drive controller 16 configured to receive position information from one or more position sensing devices (described in more detail below) in order to determine a position and orientation of the base assembly 8 and structures of the mobile imaging system coupled thereto. Based on the position of the base assembly and further based on user input (e.g., received from a user input device, such as a drive handle, keyboard, remote control, or other device), the drive controller 16 may adjust/activate the one or more motors to move the mobile imaging system 1 to a desired position.

The base assembly may thus be an automated programmable device and may be associated with a drive controller operable to compute a trajectory or path for the mobile imaging system relative to predefined trajectories. The drive controller, that may be embedded either within the mobile imaging system as shown or within a remote control console, is also operable to compute a current position of the mobile imaging system, in order to allow the mobile imaging system 1 to be located precisely in the operating room and, notably, relative to the examination table 10.

Therefore, according to predetermined pathways and/or under the control of the user input device that can be operated by an operator, the mobile imaging system is capable of being moved automatically in the operating room.

This is in particular the case, notably, during the positioning of the x-ray imager facing the examination table, in order to place the tube 2 and the detector 4 facing a region of interest to be radiographed or during the movement of the mobile imaging system to an out-of-the-way waiting position when it is no longer in use.

For example, the drive controller 16 may compute the current position of the mobile imaging system, and in particular the position of the imaging assembly to generate signals that may be sent to the motor(s) of the mobile device to steer the base assembly relative to the optimal or pre-programmed trajectory or path.

The mobile imaging system 1 may include an arm 13 erected from the support 7, for example, and in which are located a set of connection elements. Such connection elements may comprise a set of power and electrical connection cables dedicated to supply the apparatus with electric power, of ducts in which a cooling fluid circulates, for example water, and of data transmission channels, for example of the optical fiber type. The set of connection elements may be connected to a remote cabinet, situated in a remote equipment room, for example.

The connection elements may be placed in a retractable arm 14 which may include a chain of articulated links adapted to confine the bundle of connection elements in a horizontal plane, and situated in the vicinity of the ceiling of the operating or examination room, for example. The retractable arm 14 is connected, at one end, to the erected arm 13 and, at the opposite end, to a fixed attachment element 15, for example mounted on the wall and/or ceiling of the operating room.

For example, the retractable arm 14 may be provided with a set of chain links each articulated with each other, so that when the base assembly and, consequently, the mobile imaging system 1 is moved across the floor, the deformation of the chain occurs. The retractable arm 14 may comprise structures other than a chain, such as a telescoping arm. It should be appreciated that the mutually opposite ends of the retractable arm 14 are jointed to the attachment element 15 and to the arm 13, respectively.

In order to determine its current position, the mobile imaging system 1 is provided with a localization system associated with the drive controller. The localization system includes a plurality of position sensing devices, described in more detail herein.

The localization system comprises a first angular sensor, a second angular sensor, and a linear sensor coupled between the first angular sensor and the second angular sensor. The first angular sensor may be coupled to a fixed reference point, such as the attachment element 15, and may be configured to measure a first angle of rotation of the linear sensor relative to the reference point. The second angular sensor may be coupled to the mobile imaging system and may be configured to measure a second angle of rotation of the linear sensor relative to the mobile imaging system. The linear sensor may be configured to measure a distance between the reference point and the mobile imaging system. Based on the first angle of rotation, second angle of rotation, and distance, the drive controller may determine a position in x,y space of the mobile imaging system relative to the reference point as well as an orientation of the mobile imaging system relative to the reference point, as explained in more detail below. The angular sensors may include suitable angle-sensing mechanisms, including but not limited to rotary encoders, laser or other optical sensors, accelerometers, and so forth. The linear sensor may include suitable a distance-sensing mechanism, including but not limited to a string encoder, a linear variable differential transducer, a position transmitter, and so forth.

Thus, as shown in FIG. 1, the localization system includes a first angular sensor in the form of a first rotary encoder 17, a second angular sensor in the form of a second rotary encoder 18, and a linear sensor in the form of a string encoder 19. The localization system is positioned beneath the retractable arm 14. The first rotary encoder may be jointed to the attachment element 15 and the second rotary encoder may be jointed to the erected arm 13. The string encoder 19 is coupled to the first rotary encoder 17. The string encoder 19 includes a string 20 coupled to the second rotary encoder 18.

The localization system is effectively mounted on the attachment element 15 and on the erected arm 13 via two pivot axes A and A' such that when the mobile imaging system is moved by the mobile device of the base assembly across the floor, a shift of the angle of rotation around the pivot axis A as well as a shift of the angle of rotation of the apparatus around the pivot axis A' may occur. In addition, the angle formed by the string 20 relative to the second rotary encoder 18 varies according to the movement of the mobile imaging system 1.

The first rotary encoder 17, second rotary encoder 18, and string encoder 19 are each communicatively coupled to drive controller 16. As such, the information obtained by each of first rotary encoder 17, second rotary encoder 18, and string encoder 19 is sent to drive controller 16. Drive controller 16 is configured to determine a position of the mobile imaging system 1 in a Cartesian coordinate system of the room in which apparatus 1 is installed based on the output from first rotary encoder 17, second rotary encoder 18, and string encoder 19. For example, drive controller 16 may include non-transitory memory storing instructions that are executable by a processor of drive controller 16. The instructions may include instructions to calculate a position of the mobile imaging system 1 based on output received from first rotary encoder 17, second rotary encoder 18, and string encoder 19.

The first rotary encoder 17 and second rotary encoder 18 may be suitable encoders, such as conductive, optical, or magnetic. The string encoder may include string 20 (which may be a suitable wire or string) wound on a drum and an encoder to detect rotation of the drum as the string is wound or unwound. The encoder of the string encoder may be conductive, optical, or magnetic. In some examples, the string 20 is comprised of stainless steel, and the string encoder 19 may be configured to provide a pull force of 10N to 13.5N, at least in some examples.

Figure 2:
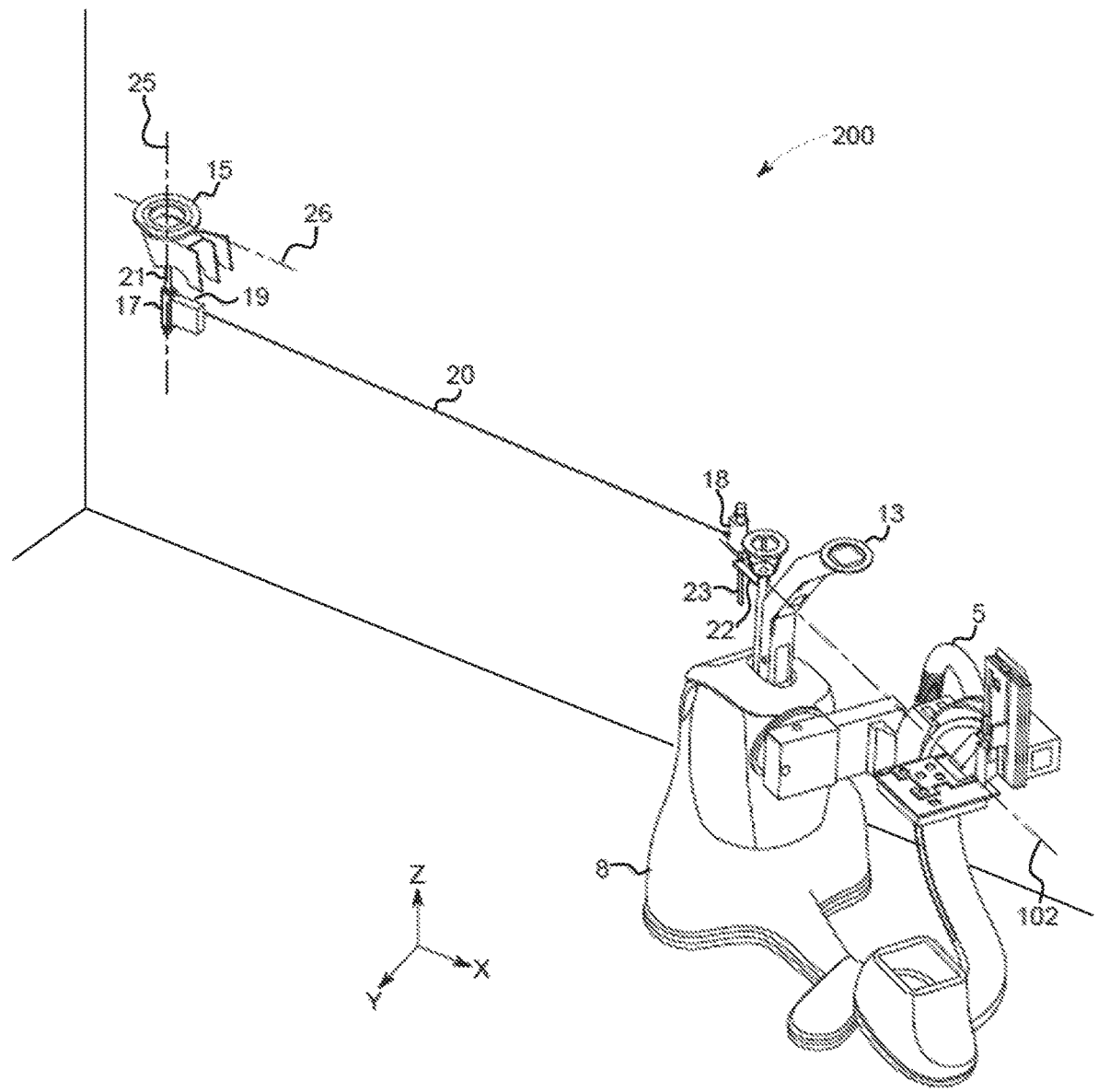
FIG. 2 shows a top perspective view of the mobile imaging system of FIG. 1.

FIG. 2 shows a top perspective view 200 of the mobile imaging system 1 of FIG. 1 with the retractable arm 14 removed for clarity. As shown in FIG. 2, the attachment element 15 is configured to mount to a ceiling (also removed for clarity) of a room. The first rotary encoder 17 is coupled to the attachment element 15 via a first rod 21 (described in more detail below with respect to FIGS. 3 and 4) and the string encoder 19 is coupled to the first rotary encoder 17. The first rod 21 may extend along a first axis 25 that is parallel to the z axis of FIG. 2. The first axis 25 may be a rotational axis of the first rotary encoder 17 (e.g., equivalent to the pivot point A of FIG. 1). A second axis 26 may be perpendicular to the first axis 25 and parallel to the x axis of FIG. 2. The second axis 26 may be a reference axis that is defined by the room, attachment element 15, and/or other non-moving components, and the position of the mobile imaging system may be determined relative to both first axis 25 and second axis 26, as explained in more detail below.

The string 20 of the string encoder 19 is coupled to the second rotary encoder 18. The second rotary encoder 18 is coupled to erectable arm 13 via a rotatable joint 22. The rotatable joint 22 is configured to move linearly along with the erectable arm 13 and base assembly 8, in the x and y directions, as well as move rotationally as the orientation of the mobile imaging system changes (e.g., as central axis 102 changes). The second rotary encoder 18 is rotationally coupled around a second rod 23. The second rod 23 may be coupled to the rotatable join 22 and may rotate relative to the second rotary encoder 18 when the orientation of the mobile imaging system 1 is changed. The second rotary encoder 18 is configured to measure the angle of rotation of the mobile imaging system (e.g., the angle of rotation of central axis 102 relative to the string 20) as the second rod 23 rotates.

Figure 3:
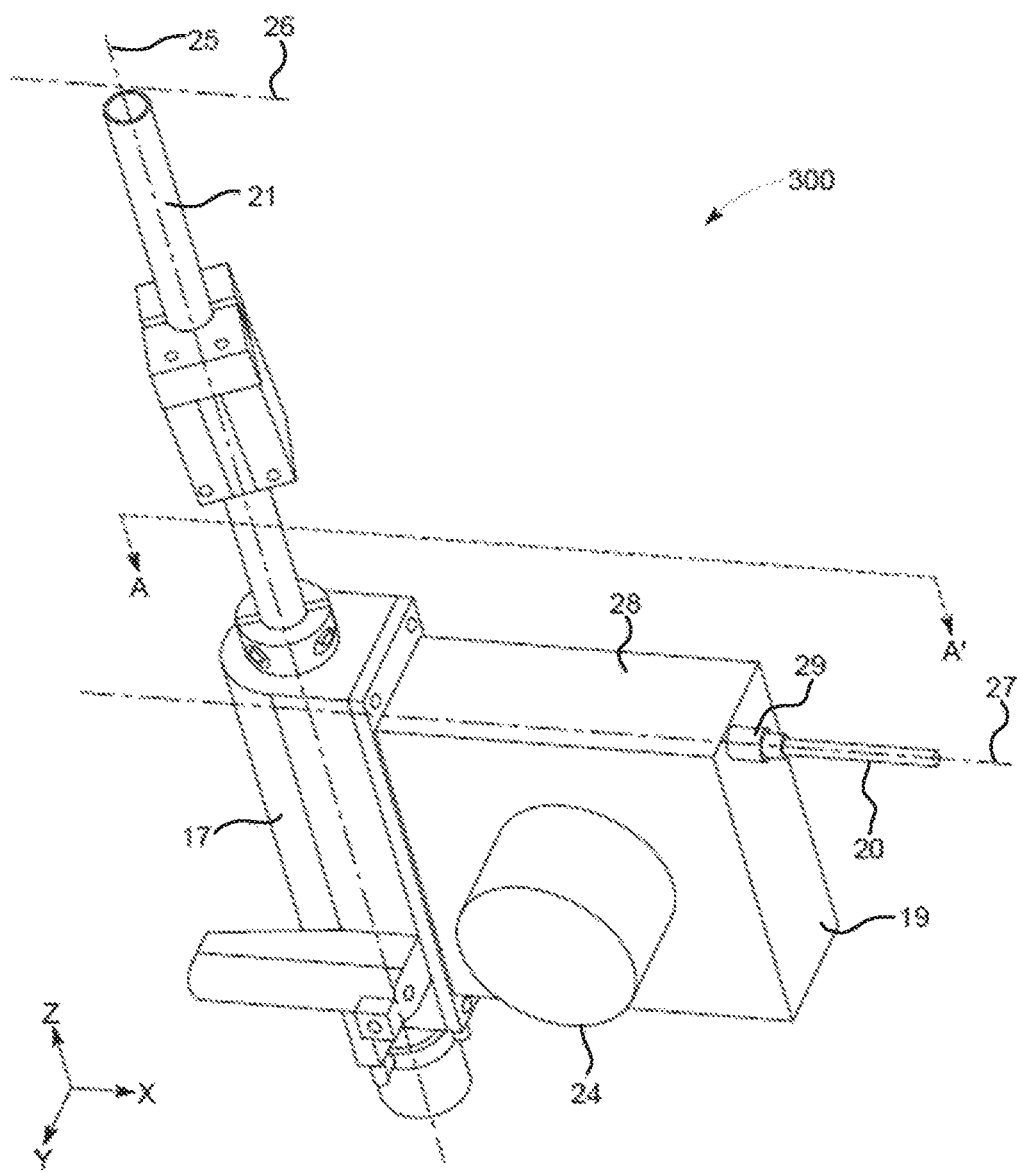
FIG. 3 shows a magnified view of a rotary encoder coupled to a string encoder.
Figure 4:
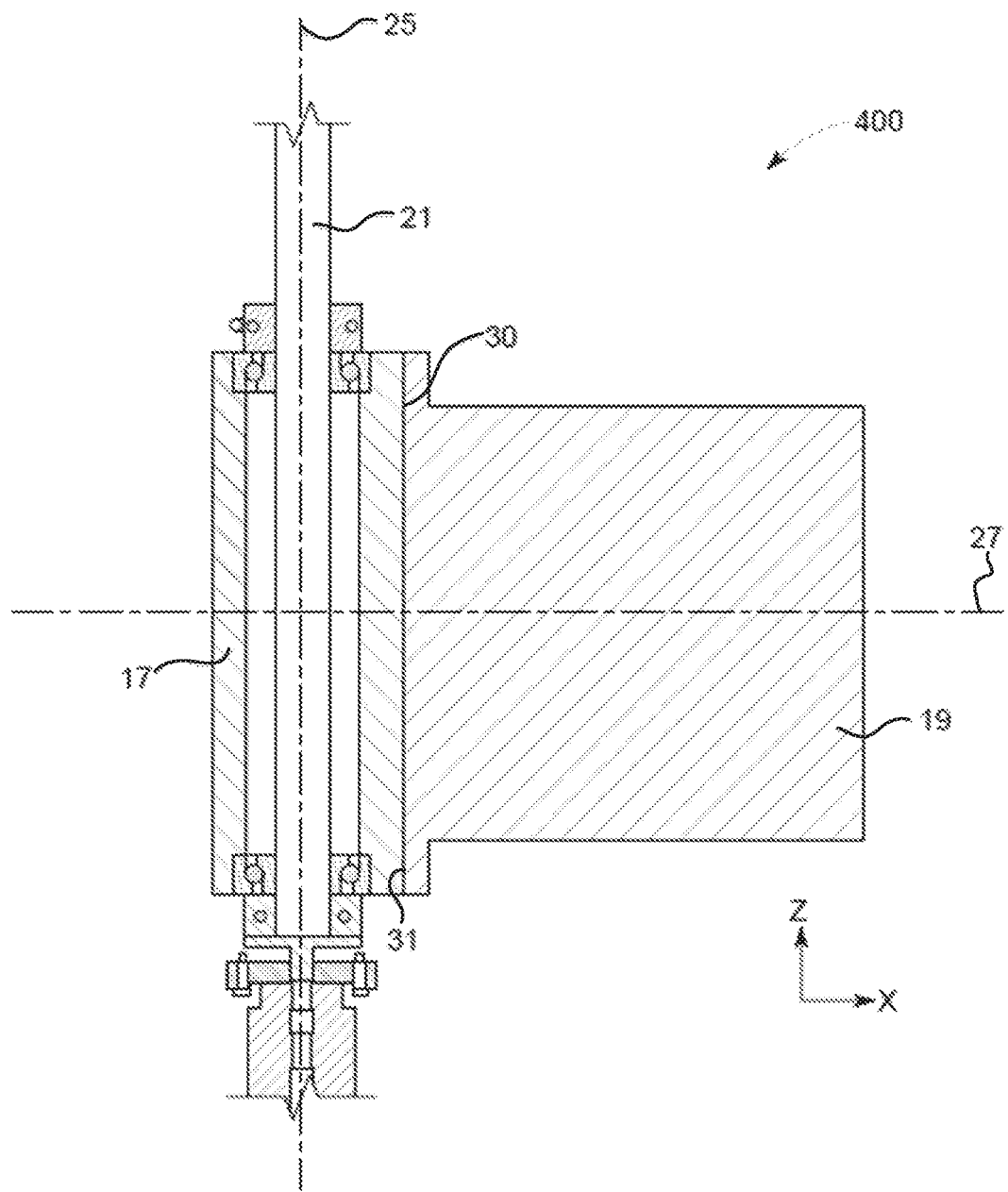
FIG. 4 shows a cross-sectional view of the rotary encoder and string encoder of FIG. 3.

FIG. 3 shows a magnified view 300 of the first rotary encoder 17 and the string encoder 19. FIG. 4 shows a cross-sectional view 400 of the first rotary encoder 17 and string encoder 19 taken across line A-A' of FIG. 3. As shown, the first rotary encoder 17 is rotationally coupled around the first rod 21. The first rod 21 may remain fixed in place as the mobile imaging system moves, and the first rotary encoder 17 may move in a rotational manner around the first rod 21 (e.g., around a rotational axis of the first rod 21, which may be the first axis 25) as the mobile imaging system moves. The first rotary encoder 17 may measure the first angle of rotation (of the string encoder relative to a reference point, herein the second axis 26) as the first rotary encoder 17 rotates around the first rod 21. The first rotary encoder 17 may rotate due to movement of the string encoder 19, which is directly coupled to (e.g., in face-sharing contact with) the first rotary encoder 17.

The string encoder 19 includes a housing 28 housing the string 20, which is wound around a drum 24 extending outward from the housing 28. The string 20 may exit the housing 28 at outlet 29. While not shown in FIGS. 3 and 4, an opposite end of string 20 is coupled to the second rotary encoder 18. The string 20 may extend along a third axis 27, also referred to as a string axis of the string encoder. The third axis 27 intersects the rotational axis (e.g., first axis 25) of the first rotary encoder 17. The third axis 27 may change as the mobile imaging system moves and the string encoder 19 and first rotary encoder 17 rotate about the first rod 21. The first rotary encoder 17 may measure the angle of rotation of the third axis 27 relative to the second axis 26.

The housing 28 of the string encoder 19 includes a coupling surface 30 that extends along a plane parallel to the first axis 25. The coupling surface 30 is in face-sharing contact with a complementary coupling surface 31 of the first rotary encoder 17. In some examples, the coupling surface 30 may be in face-sharing contact with the complementary coupling surface 31 along an entirety of the coupling surface 30. Further, in the cross-section shown in FIG. 4, the housing 28 has a substantially square shape, and the coupling surface 30 may extend beyond the square shape of the housing so that the coupling surface 30 may be equal in length to the complementary coupling surface 31 of the first rotary encoder 17. The outlet 29 may be positioned on a surface opposite of coupling surface 30.

To ensure measurement accuracy, the string may be maintained under a suitable tension (e.g., a pull force to cause the string to unwind from the drum as the mobile imaging system moves may be in a range of 10N to 13.5N) such that the string remains straight and does not sag or otherwise change shape as the mobile imaging system moves away from the first rotary encoder and string encoder complex. By positioning the string encoder 19 relative to the first rotary encoder 17 in the manner described above, the measurement accuracy of the first rotary encoder and string encoder may be increased and any pull force acting on the string may not affect the first rotary encoder. For example, by configuring the string encoder relative to the first rotary encoder such that the string axis of the string encoder intersects the rotational axis of the first rotary encoder, the mechanical stability of the first rotary encoder and string encoder may be increased, which may reduce bending forces acting on the first rod 21 caused by movement of the mobile imaging system (and hence tensioning of the string 20). By reducing the bending forces, measurement accuracy may be increased. These bending forces may be further reduced due to the vertical elongation of the first rotary encoder (which may have a length along the z axis that is larger than a width along the x axis or depth along the y axis) along the rotational axis and due to the string encoder being in face-sharing contact along some or all of the vertical length of the first rotary encoder. The extensive nature of the face-sharing contact between the first rotary encoder and string encoder, as well as the face-sharing contact extending along the rotational axis, increases the thermal and mechanical stability of the first rotary encoder and string encoder complex, which reduces bending forces relative to other mechanisms by which the first rotary encoder and string encoder could be coupled, and thus increases measurement accuracy.

Figure 5:
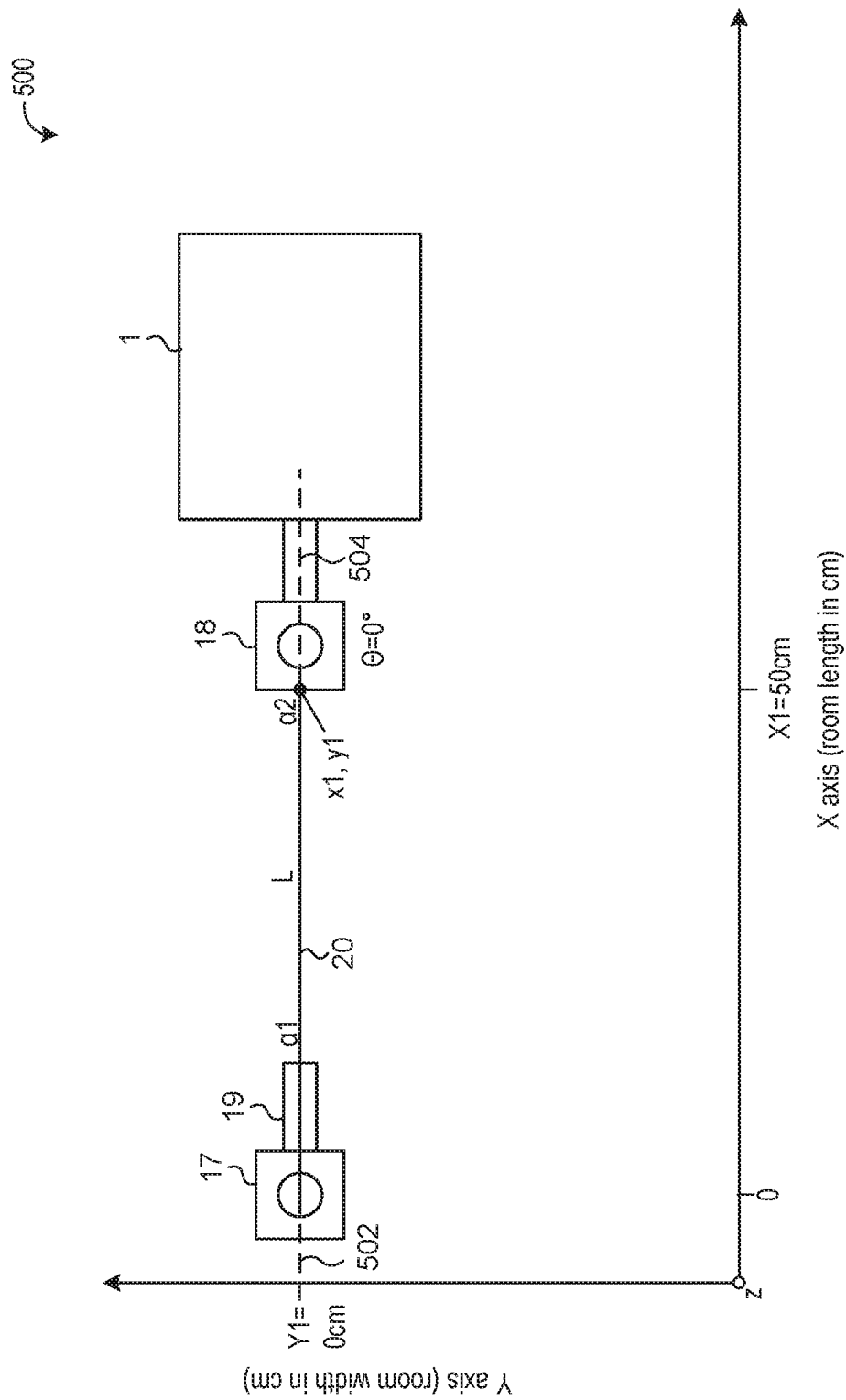
FIGS. 5-7 schematically show the mobile imaging system in a plurality of different positions.
Figure 6:
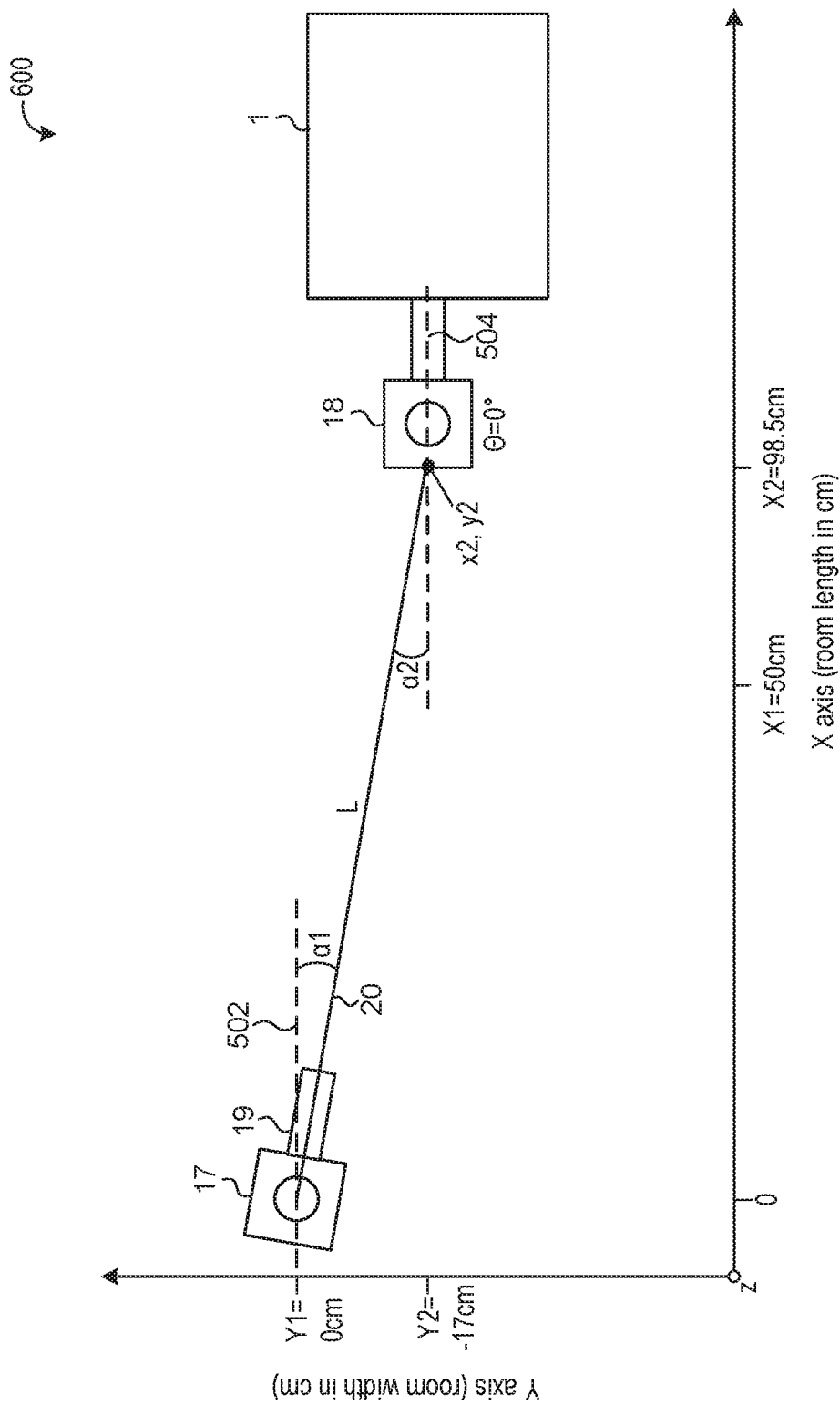
Figure 7:
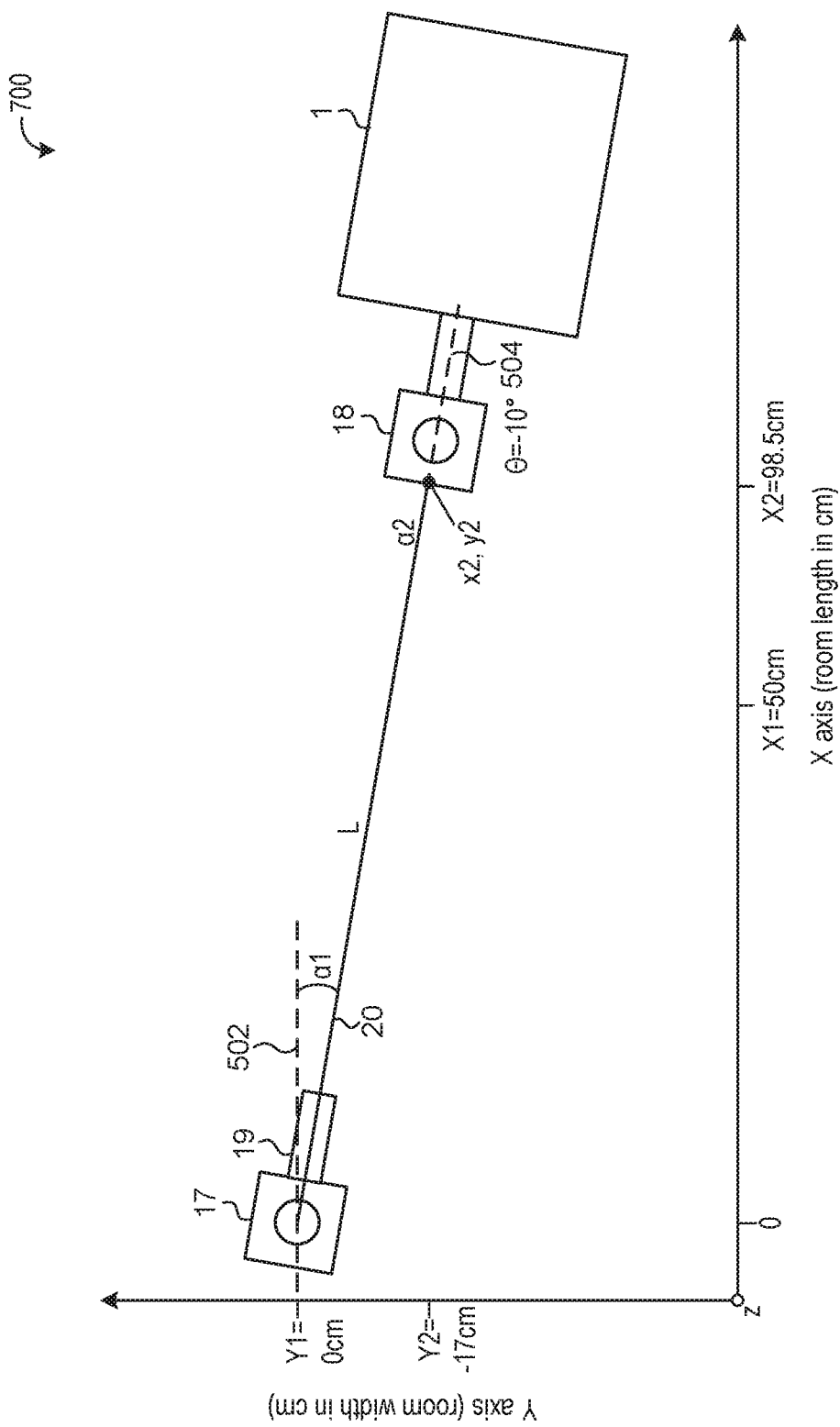

FIGS. 5-7 schematically show the mobile imaging system 1 and localization system in a top-down view in a first position 500 (shown in FIG. 5), a second position 600 (shown in FIG. 6), and a third position 700 (shown in FIG. 7) in the same room with the same set of Cartesian coordinates. In the examples shown in FIGS. 5-7, the coordinate system includes an x axis that corresponds to the length of the room (in cm) and a y axis that corresponds to the width of the room (in cm). Referring first to FIG. 5, the first position 500 may correspond to a parked or home position for the mobile imaging system 1. In the first position 500, the mobile imaging system may be as close as possible to the attachment element 15, e.g., the retractable arm 14 may be fully retracted. Further, in the first position 500, a center point of the mobile imaging system 1 (which may be defined by a point where the second arm 6 couples to the fixed support 7, for example, or which may be defined by the center point between the drive wheels 11) lies along a first reference axis 502, where the first reference axis 502 is an axis defined by the attachment device 15 or other non-moving component or position. For example, the first reference axis 502 may be parallel to the x axis of the coordinate system and may be a central longitudinal axis of the attachment element 15. The first reference axis 502 may be the second axis 26 of FIGS. 2-3. When the apparatus is in the first position 500, a second reference axis 504 (which is defined by the mobile imaging system and thus may change position as the mobile imaging system changes position) is aligned with the first reference axis 502. The second reference axis 504 may be the central axis 102 described above with respect to FIG. 1. An axis of the string 19 (such as third axis 27 described above with respect to FIG. 3) is also aligned with first reference axis 502 and second reference axis 504.

First rotary encoder 17 may output rotational information indicative of an angle of rotation of the string encoder 19 relative to the first reference axis (e.g., an angle of third axis 27 relative to first reference axis 502). The string encoder 19 may output distance information indicative of a length between the first rotary encoder 17 (and hence the attachment element 15, which is fixed in place in a known location) and the second rotary encoder 18 (which is mounted to the mobile imaging system 1 and hence is indicative of where the mobile imaging system is positioned length-wise, relative to the attachment element 15). The second rotary encoder 18 may output rotational information indicative of an angle of rotation of the string 20 relative to the second reference axis (e.g., of third axis 27 relative to second reference axis 504). In the first position 500, the first rotary encoder 17 may output an angle $\alpha 1$ of 0° and the second rotary encoder 18 may output an angle $\alpha 2$ of 0°. The string encoder 20 may output a length (L) that represents the distance from the first rotary encoder to the second rotary encoder at the fully retracted length of the retractable arm, such as 50 cm. The position of the mobile imaging system 1 may be determined based on the output of the two rotary encoders and the string encoder. The position may include x,y coordinates (e.g., x,y coordinates of where the string couples to the second rotary encoder) and an orientation ($\Theta$) of the mobile imaging system relative to the first reference axis. The position may be calculated based on the following equations:

$$X = L^* \cos(\alpha 1)$$

$$Y = L^* \sin(\alpha 1)$$

$$\Theta = \alpha 1 + \alpha 2$$

For L=50 cm, $\alpha 1$=0°, and $\alpha 2$=0°, the position of the mobile imaging system 1 in x,y coordinates may be (50, 0) and the orientation may be 0° relative to the first reference axis 502.

FIG. 6 shows the mobile imaging system in a second position 600. In the second position 600, the mobile imaging system has been moved along both the x axis and y axis relative to the first position 500, but the orientation of the mobile imaging system relative to the first reference axis 502 has not changed. Thus, the first rotary encoder may output an angle $\alpha 1$ of −10°, the second rotary encoder may output an angle $\alpha 2$ of 10°, and the string encoder may output a length L of 100 cm. Using the above equations, the position of the mobile imaging system in x,y coordinates may be (98.5, −17) and the orientation of the mobile imaging system may be 0°.

FIG. 7 shows the mobile imaging system in a third position 700. In the third position 700, the mobile imaging system is in the same position along both the x axis and y axis relative to the second position 600, but the orientation of the mobile imaging system relative to the first reference axis 502 has changed. Thus, the first rotary encoder may output an angle $\alpha 1$ of −10°, the second rotary encoder may output an angle $\alpha 2$ of 0°, and the string encoder may output a length L of 100 cm. Using the above equations, the position of the mobile imaging system in x,y coordinates may be (98.5, −17) and the orientation of the mobile imaging system may be −10° relative to the first reference axis.

Thus, each of the first rotary encoder 17, second rotary encoder 18, and string encoder 19 may output position information to the drive controller 16. The drive controller 16 may calculate the position of the mobile imaging system in x,y space relative to a fixed reference point (e.g., relative to the attachment element 15) based on the output of the first rotary encoder 17 and the output of the string encoder 19. The drive controller 16 may calculate the orientation of the mobile imaging system relative to the fixed reference point based on the output of the first rotary encoder 17 and the second rotary encoder 18. When the drive controller 16 receives a command to move the mobile imaging system 1, the drive controller 16 may move the mobile imaging system 1 by activating/adjusting the drive and/or steering motors. The drive and/or steering motors may be adjusted based on the currently calculated position of the mobile imaging system 1 and the commanded position of the mobile imaging system. For example, the drive controller 16 may determine a respective velocity for each of the drive wheels and/or a respective steering angle for each of the drive wheels based on the current position and commanded position of the mobile imaging system, and adjust the drive motor(s) and/or steering motor accordingly. As the mobile imaging system 1 is moved, the drive controller 16 may continuously or periodically determine the current position of the mobile imaging system 1 based on the output of the rotary encoders and string encoder.

While FIGS. 1-7 are described above with respect to a mobile imaging system including an x-ray imager, other imaging modalities are possible. For example, fixed support 7 may be coupled to a suitable imaging assembly that includes components of an x-ray imager (as described above), an ultrasound imager, a visible light imager (e.g., camera), or other imaging modality.

Figure 8:
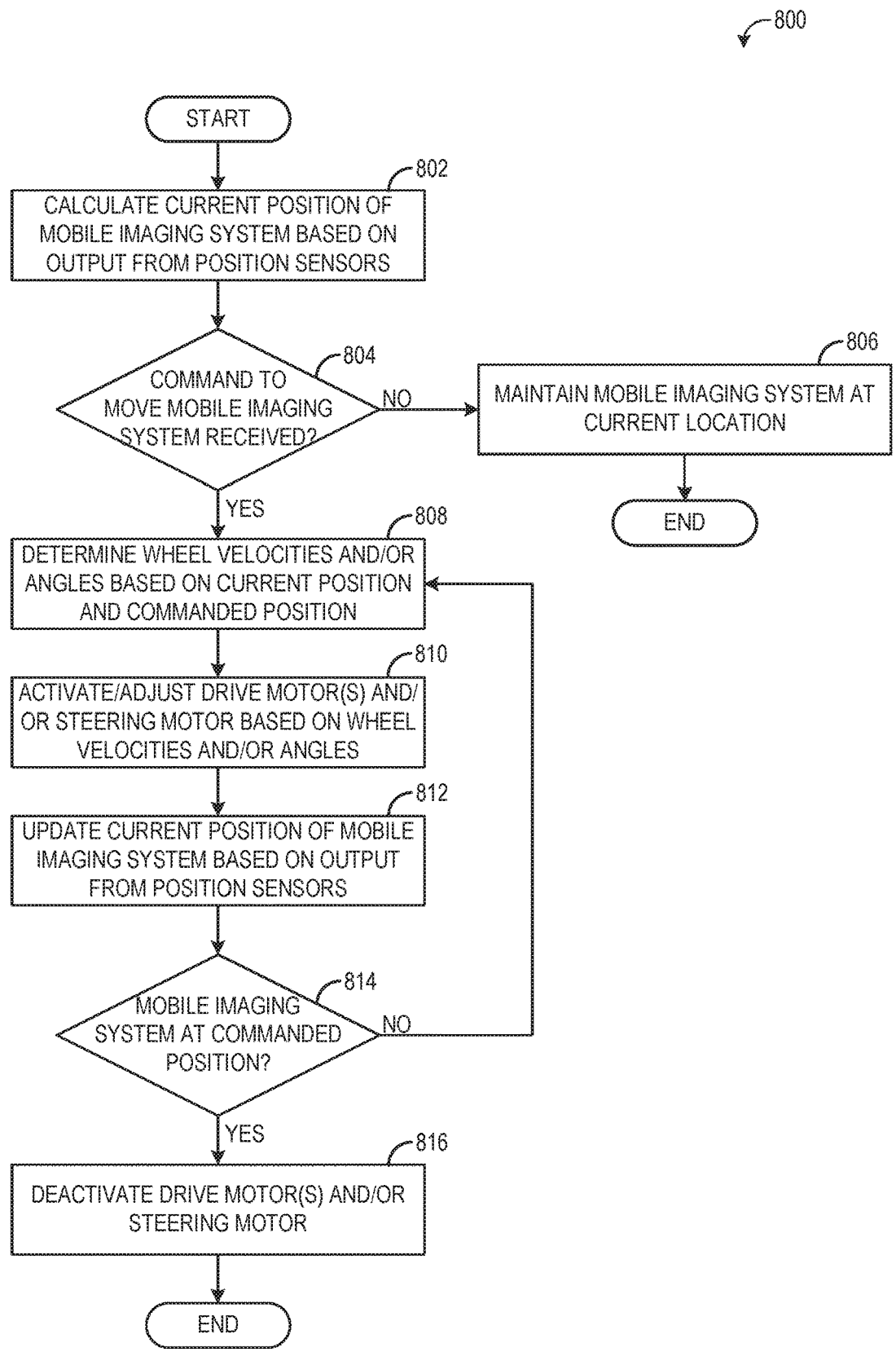
FIG. 8 is a flow chart illustrating a method for moving a mobile imaging system.

FIG. 8 is a flow chart illustrating a method 800 for moving a mobile imaging system, such as the mobile imaging system 1 described above with respect to FIG. 1. The mobile imaging system may include an imaging modality, such as an x-ray system as described above, coupled to a movable platform. The movable platform may include drive wheels, one or more drive motors configured to drive the drive wheels, one or more steering motors configured to adjust respective angles of the drive wheels, a drive controller, and a localization system including a plurality of position sensors. For example, the position sensors may include a first rotary encoder (e.g., encoder 17) coupled at a rotatable joint between a fixed element (such as attachment element 15)

and a movable component of the mobile imaging device (such as retractable arm 14). The position sensors may further include a second rotary encoder (e.g., encoder 18) coupled to the mobile imaging device at a rotatable joint (such as coupled to erectable arm 13 where erectable arm 13 rotatably couples to retractable arm 14) and a string encoder (e.g., encoder 19). The string encoder may be coupled to the first rotary encoder and include a string (e.g., string 20) that extends between the string encoder and the second rotary encoder.

Method 800 may be executed by a controller (e.g., drive controller 16 shown in FIG. 1) based on instructions stored on a memory of the controller and in conjunction with signals received from sensors of the mobile imaging system, such as the rotary encoders and string encoder described above with reference to FIGS. 1-7. The controller may employ actuators of the mobile imaging system (e.g., the drive wheels, which may be driven by one or more electric motors) to move the mobile imaging system, according to the methods described below.

At 802, the current position of the mobile imaging system is calculated based on the output from the position sensors. For example, as explained above with respect to FIGS. 5-7, the position of the mobile imaging system (e.g., the position of the imaging assembly and/or movable platform (e.g., base assembly) to which the imaging assembly is coupled) in 2D space as well as the orientation of the mobile imaging system relative to a reference axis may be determined from the output of the first rotary encoder, second rotary encoder, and string encoder coupled between the first rotary encoder and second rotary encoder. The first rotary encoder may output a first angle measurement representing an angle ($\alpha 1$) between a first reference axis and a reference point of the mobile imaging system. The first reference axis may be a fixed axis and may traverse the attachment element that couples the retractable arm of the mobile imaging system to a fixed location in the room housing the mobile imaging system, such as a ceiling or wall. However, in other examples, the mobile imaging system may be capable of operating at least part of the time without a fixed attachment point to an element of the room (other than the coupling of the second rotary encoder of the mobile imaging to the string encoder and first rotary encoder). In such cases, the first reference axis may be based on the first rotary encoder and/or string encoder, such as an axis that is perpendicular to a rotational axis of the first rotary encoder. In other words, the first rotary encoder may remain in a fixed position in the room and may be coupled to the second rotary encoder located on the mobile imaging system via the string encoder, even if the mobile imaging system itself is not attached to a wall or ceiling of the room. In either case, the first reference axis may be parallel to an x axis of the room in which the mobile imaging system is installed, where the x axis is a width or length of the room. The reference point of the mobile imaging system may be a point where the string of the string encoder couples to the second rotary encoder.

The second rotary encoder may output a second angle measurement representing an angle ($\alpha 2$) between a second reference axis and the string of the string encoder. The second reference axis may be an axis of the mobile imaging system, such as a lateral axis that is parallel to the ground on which the mobile imaging system rests and which bisects the drive wheels and/or fixed support of the movable platform of the mobile imaging system (such as central axis 102 shown in FIG. 1). The string encoder may output a length measurement representing a length (L) between the first rotary encoder and the second rotary encoder.

Based on the first angle measurement and the length measurement, the drive controller of the mobile imaging system may calculate the position of the mobile imaging system in 2D space of the room. As used herein, 2D space refers to an x-y plane of the room in which the mobile imaging system is housed, where the x-y plane is defined by the length and width of the room. In other words, the drive controller determines the position of the mobile imaging system with respect to the directions of movement of the mobile imaging system (e.g., along the length and width of the room), but does not determine the position with respect to the height of the room, as the height of the mobile imaging system is fixed. The position in 2D space may be determined relative to the position of the first rotary encoder, e.g., a center point of the first rotary encoder may represent a distance of zero along both the y-axis and the x-axis.

To calculate the x,y position of the mobile imaging device in 2D space, the length may be set as the hypotenuse of a right triangle, and using the angle $\alpha 1$, the drive controller may calculate the length of the opposite side (to determine the x coordinate) and the length of the adjacent side (to determine the y coordinate) of the right triangle, using the equations $x=L^*\cos(\alpha 1)$ and $y=L^*\sin(\alpha 1)$. As the mobile imaging device may also rotate around a pivot point at the second rotary encoder, the second angle measurement may be added to the first angle measurement to determine the orientation of the mobile imaging system relative to the first reference axis. Thus, the position of the mobile imaging device calculated based on the output of the position sensors includes x,y coordinates relative to the position of the first rotary encoder and an orientation of the mobile imaging device relative to a first reference axis defined by the first rotary encoder/attachment element.

At 804, method 800 includes determining if a command to move the mobile imaging system has been received. The mobile imaging system may include one or more user input devices (e.g., keyboard, drive handle/joystick, control buttons) via which an operator of the mobile imaging system may input a command to move the mobile imaging system. The command to move the mobile imaging system may include a command to move the mobile imaging system to one of a plurality of predetermined positions. For example, the predetermined positions may include a front of an examination table (on which a patient to be imaged may be disposed), each side of the examination table, the back of the examination table, near the examination table but spaced apart from the table (e.g., to enable a clinician to access the patient, but yet allowing the mobile imaging system to quickly reach the patient when commanded), a home or parked position, and so forth. The predetermined positions may be defined by x,y coordinates relative to the first rotary encoder/attachment element and orientation of the mobile imaging system relative to the first reference axis, and may be stored in memory of the drive controller. In some examples, rather than a command to move the mobile imaging system to a predetermined position, the command to move the mobile imaging system may include real-time, operator-directed commands (e.g., where the user input device(s) may generate signals sent to the drive controller indicating desired direction(s) of movement input by the operator).

If a command to move the mobile imaging device is not received, method 800 proceeds to 806 to maintain the mobile imaging system at the current location, and then method 800 ends. If a command to move the mobile imaging system is received, method 800 proceeds to 808 to determine wheel velocities and/or angles based on the current position of the mobile imaging system (as determined based on the output from the position sensors) and the commanded position received via user input. For example, the drive controller may determine a path for the mobile imaging system, including distance and steering angle(s), to move the mobile imaging system from the current position to the commanded position, and calculate wheel velocities and/or angles to move the mobile imaging system along the path. For example, if the mobile imaging system is configured with a differential speed steering system (e.g., where the mobile imaging system is configured to turn or move along an angle based on the drive wheels operating at different velocities), the respective wheel velocities may be determined based on the calculated path, in order to steer the mobile imaging system along the path. If the mobile imaging system includes a steering mechanism to turn the drive wheels (such as a steering motor), the angles of the drive wheels may be determined based on the determined path.

At 810, method 800 includes activating and/or adjusting the drive motor(s) and/or steering motor based on the determined wheel velocities and/or angles. For example, if the mobile imaging device includes the differential speed steering system, each drive wheel may be coupled to a respective drive motor, and each drive motor may be activated and operated in order to propel the drive wheels at the determined velocities. If the mobile imaging system includes a steering motor, for example, the steering motor may be operated to adjust the angle of the drive wheels to the determined angles. The mobile imaging system may be propelled at a suitable speed, which may be predetermined and/or may be based on the distance the mobile imaging system is being moved.

At 812, the current position of the mobile imaging system is updated based on the output from the position sensors, as explained above. For example, the output from the first rotary encoder, second rotary encoder, and string encoder may be obtained by the drive controller and used to determine the current x,y position and orientation of the mobile imaging system. The position of the mobile imaging system may be updated continuously or periodically (e.g., once every second). At 814, method 800 determines if the mobile imaging system is at the commanded position, for example based on the updated current position of the mobile imaging system. If the mobile imaging system is not at the commanded position, method 800 returns to 808 to again determine the wheel velocities and/or angles based on the current position and the commanded position of the mobile imaging system, and then, if indicated, adjust the drive motor(s) and/or steering motor based on the determined velocities and/or angles. In this way, as the mobile imaging system moves along the path from the current position to the commanded position, the output from the position sensors may be used to provide real-time position updates, which the drive controller may use to recalculate the path of the mobile imaging system as the mobile imaging system moves toward the commanded position. Such an approach may provide increased accuracy in moving the mobile imaging system along the path to the predetermined position. However, in some examples, the updated current position of the mobile imaging system may only be calculated in order to determine whether the mobile imaging system is at the commanded position and thus may not be used to update the wheel velocities and/or angles as the mobile imaging system moves along the path.

If the mobile imaging system is at the commanded position, method 800 proceeds to 816 to deactivate the drive motor(s), and in some examples, deactivate the steering motor. However, when included, the steering motor may be deactivated once the drive wheels are moved to the determined angles, and may be reactivated only when a change in drive wheel angle is requested (e.g., if the path includes turns). As such, when the mobile imaging system reaches the commanded position, the steering motor may already be deactivated. Method 800 then ends.

Thus, method 800 provides for automated movement of a mobile imaging system based on a current position of the mobile imaging system and a commanded position of the mobile imaging system. The current position is determined based on output from a plurality of position sensors, including a first rotary encoder, second rotary encoder, and string encoder. The first rotary encoder may measure a first angle of rotation of the mobile imaging system (as represented by the string encoder) relative to a reference axis and the string encoder may measure a length between a reference point (herein, the first rotary encoder) and the mobile imaging system. Based on the first angle of rotation and the length, the location of the mobile imaging system in 2D space (e.g., x,y coordinates relative to the reference point) may be determined. The second rotary encoder may be measure a second angle of rotation of the mobile imaging system relative to the string encoder. Based on the first angle of rotation and the second angle of rotation, the orientation of the mobile imaging system relative to the reference point may be determined. The mobile imaging system (e.g., a drive controller of the mobile imaging system) may adjust one or more electric motors (e.g., drive motors and/or steering motors) of the mobile imaging system in order to follow a determined path from the current location and orientation of the mobile imaging system to a commanded location and orientation of the mobile imaging system (e.g., as determined form the commanded position of the mobile imaging system). The path may be determined based on the current and commanded positions of the mobile imaging system, and may be further determined based on any known obstacles in the room housing the mobile imaging system (e.g., other medical equipment).

While method 800 was described above as determining the current position of the mobile imaging system before a commanded position of the mobile imaging system is received, it is to be understood that the current position of the mobile imaging system may be determined at any suitable time, such as after a commanded position of the mobile imaging system has been received. Further, while method 800 was described above with respect to rotary encoders and a string encoder, other angular and linear position sensing mechanisms are possible.

In some examples, the current position of the mobile imaging system may be compared to a position of the mobile imaging system as determined from a secondary position sensing mechanism. For example, the mobile imaging system may include position sensors on or adjacent the drive wheels, in order to detect the angle, speed, and/or other parameters of the drive wheels. As the mobile imaging system is moved out of its home or parked position and to one or more commanded positions, the drive controller may track the current position of the mobile imaging system based on the measured drive wheel parameters. This current position may be periodically compared to the current position of the mobile imaging system determined from the angular sensors and linear sensor (as determined according to the method 800 described above, for example) in order to confirm that the position of the mobile imaging system determined from the angular sensors and linear sensor is accurate and/or rational. By periodically checking the rationality of the position determination, potential degradation or errors of the localization system may be identified and an operator of the mobile imaging system may be notified. As an example, the comparison to the drive wheel sensor determined position of the mobile imaging system may assist in detecting if an object is bending or otherwise interfering with the string of the string encoder.

FIGS. 1-7 show example configurations with relative positioning of the various components of the imaging system. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The technical effect of utilizing a linear position sensor coupled between two angular position sensors to determine a location and orientation of a mobile imaging system is reduced cost, simplified installation, and more accurate position sensing relative to other position sensing mechanisms, such as optical sensing mechanisms.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for determining a position of a mobile imaging system, the system comprising:
   a first angular sensor coupled to a reference point and configured to measure a first angle of rotation relative to the reference point;
   a linear sensor coupled between the reference point and the mobile imaging system and configured to measure a distance between the reference point and the mobile imaging system, the linear sensor coupled to the first angular sensor with a measurement axis perpendicular to and intersecting a rotational axis of the first angular sensor; and
   a second angular sensor configured to measure a second angle of rotation relative to the mobile imaging system.

2. The system of claim 1, further comprising a drive controller configured to calculate the position of the mobile imaging system based on the distance, the first angle of rotation, and the second angle of rotation.

3. The system of claim 2, wherein the drive controller is configured to determine the position of the mobile imaging system by determining coordinates of the mobile imaging system relative to the reference point based on the distance and the first angle of rotation and by determining an orientation of the mobile imaging system relative to the reference point based on the first angle of rotation and the second angle of rotation.

4. The system of claim 2, wherein the mobile imaging system includes one or more drive wheels controlled by one or more electric motors, and wherein the drive controller is configured to adjust the one or more electric motors based on the determined position of the mobile imaging system and a commanded position of the mobile imaging system.

5. The system of claim 1, wherein first angular sensor is a first rotary encoder and the second angular sensor is a second rotary encoder, and wherein the linear sensor is a string encoder.

6. The system of claim 1, wherein the mobile imaging system is coupled to an element of a room housing the mobile imaging system via a retractable arm, and wherein the reference point is a point where the retractable arm couples to the element of the room.

7. The system of claim 1, wherein the mobile imaging system comprises a movable base assembly and an imaging assembly coupled to the movable base assembly.

8. The system of claim 7, wherein the imaging assembly is an x-ray imaging assembly including an x-ray tube and an x-ray detector.

9. A mobile imaging system, comprising:
   a movable base assembly;
   an imaging assembly coupled to the movable base assembly; and
   a localization system coupled to the movable assembly and to a reference point, the localization system including a first rotary encoder, a second rotary encoder, and a string encoder coupled between the first rotary encoder and the second rotary encoder, the string encoder in face-sharing contact with the first rotary encoder along a plane parallel to a longitudinal axis of the first rotary encoder, the first rotary encoder and string encoder rotatable around the reference point.

10. The mobile imaging system of claim 9, wherein the reference point includes a rod coupled to an attachment element, the attachment element coupled to the movable base assembly via a retractable arm and configured to couple to a wall or ceiling of a room housing the mobile imaging system.

11. The mobile imaging system of claim 10, wherein the first rotary encoder is configured to rotate about the longitudinal axis, and wherein the string encoder includes a string extending between the string encoder and the second rotary encoder along a string axis perpendicular to the longitudinal axis.

12. The mobile imaging system of claim 9, further comprising a drive controller storing instructions in non-transitory memory executable by a processor to determine a current position of the movable base assembly based on output from the first rotary encoder, second rotary encoder, and string encoder.

13. The mobile imaging system of claim 12, wherein the instructions are executable to determine the current position of the mobile imaging system by:
determining coordinates of the mobile imaging system relative to the reference point based on a distance between the first rotary encoder and second rotary encoder and a first angle of rotation of the string encoder; and
determining an orientation of the mobile imaging system relative to the reference point based on the first angle of rotation and a second angle of rotation of the mobile imaging system.

14. The mobile imaging system of claim 13, wherein the distance is based on output from the string encoder, the first angle of rotation is based on output from the first rotary encoder, and the second angle of rotation is based on output from the second rotary encoder.

15. A method for adjusting a location of a mobile imaging system, comprising:
measuring a first angle of rotation of a string encoder relative to a reference point, the string encoder coupled to the reference point and to the mobile imaging system;
measuring a second angle of rotation of the string encoder relative to the mobile imaging system;
measuring a length of the string encoder between the reference point and the mobile imaging system;
receiving a commanded location of the mobile imaging system; and
moving the mobile imaging system to the commanded location along a path, the path determined based on the commanded location and a current location of the mobile imaging system, the current location based on the first angle of rotation, the second angle of rotation, and the length.

16. The method of claim 15, wherein moving the mobile imaging system comprises activating one or more drive motors and/or one or more steering motors coupled to drive wheels of the mobile imaging system.

17. The method of claim 15, wherein measuring the first angle of rotation of the string encoder relative to a reference point comprises measuring the first angle of rotation with a first rotary encoder, the string encoder coupled to the reference point via the first rotary encoder.

18. The method of claim 17, wherein measuring the second angle of rotation of the string encoder relative to the mobile imaging system comprises measuring the second angle of rotation with a second rotary encoder, the second rotary encoder coupled to a string of the string encoder and coupled to the mobile imaging system.

19. The method of claim 18, further comprising, as the mobile imaging system is moved along the path, updating the current location of the mobile imaging system based on output from the first rotary encoder, second rotary encoder, and string encoder.

20. The method of claim 15, wherein the current location of the mobile imaging system comprises a position of the mobile imaging system relative to the reference point, the position determined based on the length and the first angle of rotation, and an orientation of the mobile imaging system relative to the reference point, the orientation determined based on the first angle of rotation and the second angle of rotation.

* * * * *